Dec. 24, 1963 H. FOLMAR, JR Plant Pat. 2,335
GRAPEVINE
Filed Jan. 8, 1963
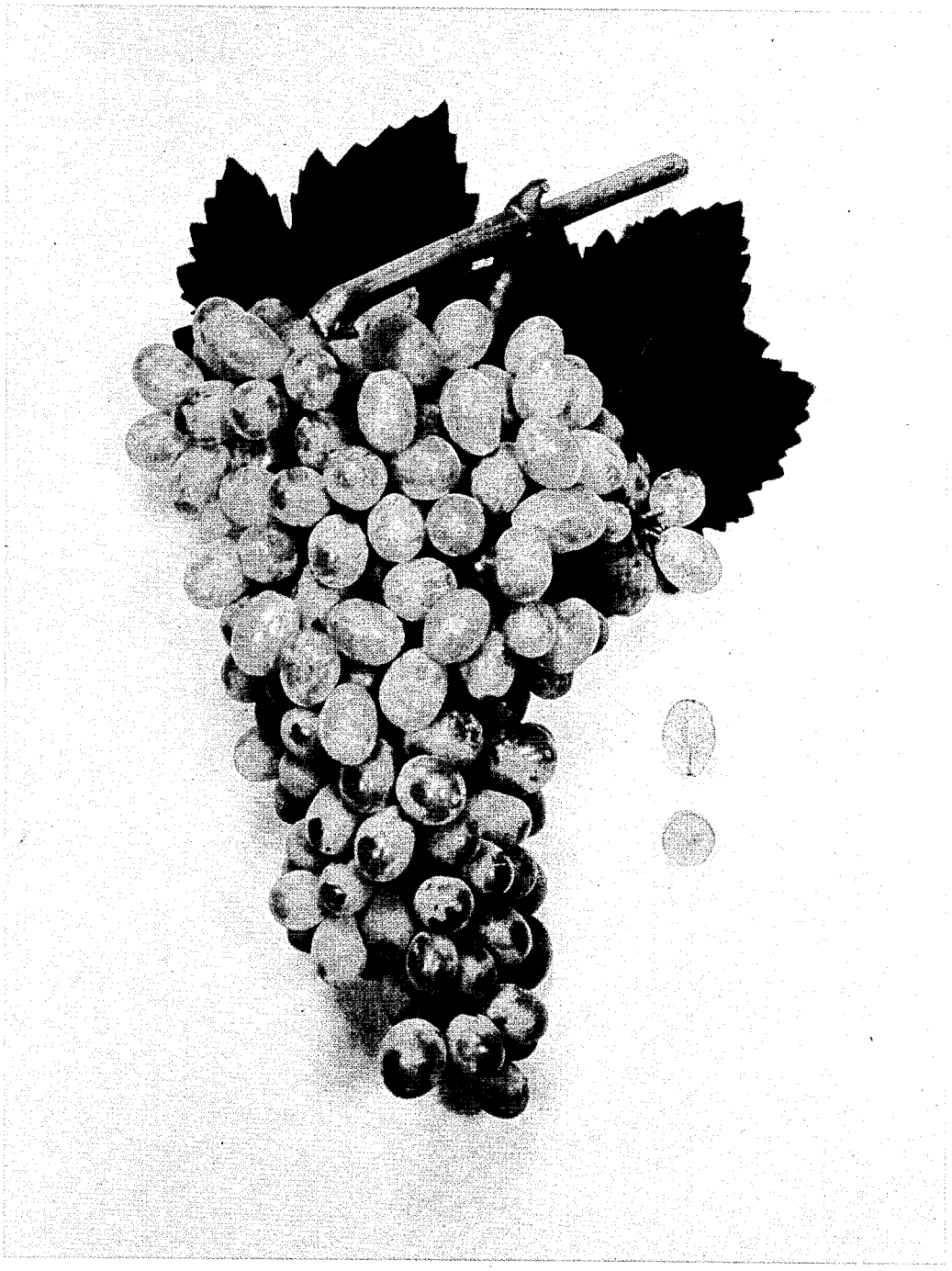
HENRY FOLMAR, JR.
INVENTOR
HUEBNER & WORREL
ATTORNEYS
BY Richard M. Worrel United States Patent Office Plant Pat. 2,335
Patented Dec. 24, 1963

2,335
GRAPEVINE

Henry Folmar, Jr., 1302 S. De Wolfe Ave., Sanger, Calif.

Filed Jan. 8, 1963, Ser. No. 250,193
1 Claim. (Cl. Plt.—47)

The present invention relates to a new and distinct variety of grapevine.

The new variety of grapevine originated in a vineyard of Delight (unpatented) grapevines maintained by the applicant at 1302 South De Wolfe, Sanger, California. The climatic conditions existing in the subject vineyard are comparable to those enjoyed by the San Joaquin Valley of central California, and include a mild winter of light rainfall (approximately 10 inches) and a hot, dry summer. During the maintenance of said vineyard, the new variety was recognized as a chance variation, or mutation, growing on a single Delight vine which it most nearly resembles. However, among other features, the fruit of the new variety can readily be distinguished from that of the Delight. In general appearance, the berries borne by the variety of the present invention are long and ovate or ovate-cylindraceous as opposed to the nearly pointed berry of the Delight. Further, they are uniformly seedless.

When originally discovered, it was noticed that the new variety bore fruit more nearly resembling that of the Thompson seedless grape (unpatented) than the Delight. However, the berry clusters of the new variety are large and well-filled but much looser than the Thompson or Delight grape clusters which enables the new variety more readily to adapt to girdling and hormone treatment for further increasing the size of the berries. With or without such size stimulating treatment, the berries are much larger, usually twice as large as those of the Thompson when subjected to the same treatment. The skin of the berries is brighter yellow than the Delight and its skin is somewhat tougher and resists puncturing better than the Thompson. It is characterized by a firm crisp berry flesh of approximately the same color as the skin. Furthermore, the fruit of the new variety ripens approximately three weeks earlier than the Thompson. To illustrate the early ripening characteristic of the new variety, a sugar content of 20 to 24 degrees Balling is achieved by the berries of the new variety at a point in time during the growing season approximately three weeks in advance of the Thompson variety achieving such a sugar content. Such earlier ripening insures a sufficient labor supply for harvesting the fruit which also has a better opportunity to completely dry with a minimum of rain hazard when used as raisins.

After having discovered the new variety as a chance variation of the Delight, the grapevine of the present invention was asexually reproduced by three cuttings from the parent plant at 1302 South De Wolfe, Sanger, California, under the direction and control of the applicant. The three cuttings subsequently produced scions for 75 grafts which grew well and exhibited vigorous and healthy qualities of growth. The fruit subsequently borne by vines from the cuttings and grafts had the same distinctive characteristics observed in the fruit of the originally discovered chance variation. The large, loose clusters of berries are typical of the fruit borne by the vines of the subject variety.

The accompanying drawing, which is an enlarged color photograph, shows leaves from a vine of the new variety along with a typical specimen bunch of grapes borne by the vine.

The following is a detailed description of the pomological characteristics of the subject grapevine. Color terminology is in accordance with that of the "Dictionary of Color," Maerz and Paul, second edition.

Where dimensions, sizes, colors and other characteristics are given, it is to be understood that such characteristics are approximations of averages set forth as accurately as practicable.

Vine: The vine is similar in characteristics to that of the Delight grapevine.

*Size.*—Large—similar to Thompson.
*Growth.*—Vigorous, but slower than Thompson.
*Productivity.*—Heavy and regular.
*Canes.*—Stout—shorter than Thompson. Joints—more closely spaced than usual. Tendrils—stout, short and abundant—like Thompson. Color—medium brown (13–K–8).

Foliage:

*Leaves.*—Number—average—similar to Thompson but greener, smaller and of less luster, being more like the Delight. Color—dark green (23–L–8).

Flowers:

*Number.*—Average.
*Blossom color.*—Pale greenish yellow varying in relation to maturity.
*Shape and size of cluster.*—Narrow and tapering, long, narrow.
*Average length of peduncle.*—3 inches.

Fruit:

*Maturity.*—Approximate dates—from about August 1 or earlier for fresh eating, and August 12 for drying or other uses requiring maximum sugar content.
*Size of berry.*—Large.
*Diameter.*—17 millimeters.
*Base to apex.*—25 millimeters.
*Average number of clusters to vine.*—25.
*Average number of berries to cluster.*—200.
*Number of seeds to berry.*—None.
*Productivity.*—Average.
*Skin.*—Tight—heavier and tougher than Thompson.
*Color.*—Skin of uniformly over-all light yellowish green from (21–J–1) to a lighter yellowish green (20–I–1). Flesh is approximately the same color as the skin.
*Ripening.*—August 1 to August 12.
*Clusters ripen.*—Evenly.
*Texture.*—Medium.
*Flavor.*—Sweet—higher sugar content than Thompson.
*Aroma.*—Delicate.
*Eating quality.*—Excellent.
*Juice quality.*—Like Thompson.
*Shipping quality.*—Excellent.
*Uses.*—Fresh table, raisins and wine.

Most unusual characteristics: Early ripening, large size, and loose clusters which can readily accommodate berry expansion from girdling or the use of hormones.

The new variety grapevine has been described as it exists under the ecological conditions prevailing in the central San Joaquin Valley of California. Normal variations can be expected under different environmental conditions.

Having thus described the instant grapevine, I claim:

A new and distinct variety of grapevine substantially as illustrated and described, characterized principally by its large seedless berries growing in large loose clusters, the fruit maturing approximately three weeks earlier than the Thompson grape, which it most nearly resembles but from which it is distinguished by its earlier maturing characteristics and its sweeter flavor.

No references cited.